United States Patent
Battaglia

(10) Patent No.: US 10,881,613 B2
(45) Date of Patent: Jan. 5, 2021

(54) FUMARATE POLYMERSOMES

(71) Applicant: UCL BUSINESS LTD, London (GB)

(72) Inventor: Giuseppe Battaglia, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 16/084,769

(22) PCT Filed: Mar. 17, 2017

(86) PCT No.: PCT/GB2017/050756
§ 371 (c)(1),
(2) Date: Sep. 13, 2018

(87) PCT Pub. No.: WO2017/158382
PCT Pub. Date: Sep. 21, 2017

(65) Prior Publication Data
US 2019/0076359 A1     Mar. 14, 2019

(30) Foreign Application Priority Data
Mar. 17, 2016  (GB) .................................. 1604553.6

(51) Int. Cl.
| A61K 9/127 | (2006.01) |
| A61P 19/02 | (2006.01) |
| A61K 31/704 | (2006.01) |
| A61K 47/34 | (2017.01) |
| A61P 37/00 | (2006.01) |
| A61P 17/06 | (2006.01) |
| A61P 35/02 | (2006.01) |
| A61P 25/00 | (2006.01) |

(52) U.S. Cl.
CPC .......... *A61K 9/1273* (2013.01); *A61K 31/704* (2013.01); *A61K 47/34* (2013.01); *A61P 17/06* (2018.01); *A61P 19/02* (2018.01); *A61P 25/00* (2018.01); *A61P 35/02* (2018.01); *A61P 37/00* (2018.01)

(58) Field of Classification Search
None
See application file for complete search history.

(56) References Cited

U.S. PATENT DOCUMENTS

| 6,384,105 B1 * | 5/2002 | He ........................... A61L 27/18 523/113 |
| 2005/0163743 A1 | 7/2005 | Lewis et al. |
| 2008/0181939 A1 | 7/2008 | Discher et al. |
| 2008/0311045 A1 * | 12/2008 | Hardy .................. A61K 9/0009 424/9.3 |
| 2009/0286247 A1 | 11/2009 | Hirao et al. |
| 2010/0003336 A1 | 1/2010 | Deming et al. |
| 2010/0226955 A1 | 9/2010 | Ludwig et al. |
| 2010/0310660 A1 | 12/2010 | Tsai et al. |
| 2010/0316706 A1 | 12/2010 | Joshi et al. |
| 2011/0065807 A1 | 3/2011 | Radovic-Moreno et al. |
| 2011/0111036 A1 | 5/2011 | Lewis et al. |
| 2011/0150941 A1 * | 6/2011 | Battaglia .............. A61K 9/0014 424/400 |
| 2011/0172240 A1 | 7/2011 | Milne et al. |
| 2012/0076730 A1 | 3/2012 | Muro Galindo et al. |
| 2015/0079180 A1 | 3/2015 | Karaborni et al. |
| 2015/0110713 A1 | 4/2015 | Manganaro et al. |
| 2019/0046445 A1 | 2/2019 | Battaglia |

FOREIGN PATENT DOCUMENTS

| EP | 2 322 227 A1 | 5/2011 |
| JP | H03-31718 B2 | 5/1991 |
| WO | 93/01221 A1 | 1/1993 |
| WO | 94/16749 A1 | 8/1994 |
| WO | 95/20407 A1 | 8/1995 |
| WO | 02/028929 A1 | 4/2002 |
| WO | 03/074090 A2 | 9/2003 |
| WO | 2006080849 A2 | 8/2006 |
| WO | 2009/061473 A2 | 5/2009 |
| WO | 2009/138472 A1 | 11/2009 |
| WO | 2009/138473 A2 | 11/2009 |
| WO | 2009/138477 A2 | 11/2009 |
| WO | 2010/148653 A1 | 12/2010 |
| WO | 2011/005098 A1 | 1/2011 |
| WO | 2011005098 A1 | 1/2011 |
| WO | 2011/116132 A1 | 9/2011 |
| WO | 2012/046994 A2 | 4/2012 |
| WO | 2013/078562 A2 | 6/2013 |
| WO | 2014/122646 A1 | 8/2014 |
| WO | 2015/059180 A2 | 4/2015 |
| WO | 2016/090111 A1 | 6/2016 |

(Continued)

OTHER PUBLICATIONS

Colley HE, Polymersome mediated delivery of combination anti-cancer therapy to head and neck cancer cells: 2D and 3D in vitro evaluation, Mol Pharmaceutics, 11, 1176-1188 (Year: 2014).*
Abbas et al. "p21 in Cancer: Intricate Networks and Multiple Activities," (2009) Nat Rev. Cancer 9, 400-414.
Abdelmoshen et al. "Formation of Well-Defined, Functional Nanotubes via Osmotically induced Shape Transformation of Biodegradable Polymersomes," (2016) J. Am. Chem. Soc. 138, 9353-9356.
Anderson "Movement of a semipermeable vesicle through an osmotic gradient," (1983) Phys. Fluids 26, 2871-2879.

(Continued)

*Primary Examiner* — Celeste A Roney
(74) *Attorney, Agent, or Firm* — Kilpatrick Townsend & Stockton LLP

(57) ABSTRACT

The present invention relates to fumarate polymersomes. The polymersomes are capable of targeting immune cells and then hydrolysing to release the immunomodulatory compound fumarate. The polymersomes can thus be used methods for the treatment of prevention of diseases, including immune diseases such as multiple sclerosis and psoriasis.

12 Claims, 3 Drawing Sheets

(56) References Cited

FOREIGN PATENT DOCUMENTS

| | | |
|---|---|---|
| WO | 2017/144849 A1 | 8/2017 |
| WO | 2017/191444 A1 | 11/2017 |
| WO | 2017/199023 A1 | 11/2017 |

OTHER PUBLICATIONS

Arnold et al. "Enrichment of Single-Walled Carbon Nanotubes by Diameter in Density Gradients," (2005) Nano Letters 5, 713-718.
Arnold et al. "Sorting carbon nanotubes by electronic structure using density differentiation," (2006) Nature Nano 1, 60-65.
Bae et al. "Safety and Efficacy Evaluation of Carnosine, an Endogenous Neuroprotective Agent for Ischemic Stroke," (2013), Stroke, 44, 205-212.
Battaglia and Ryan "Bilayers and Interdigitation in Block Copolymer Vesicles," (2005) J. Am. Chem. Soc. 127(24), 8757-8764.
Battaglia and Ryan "Effect of Amphiphile Size on the Transformation from a Lyotropic Gel to a Vesicular Dispersion," (2006) Macromolecules 39, 798-805.
Battaglia and Ryan "Neuron-Like Tubular Membranes Made of Diblock Copolymer Amphiphiles," (2006) Angewandte Chemie International Edition 45(13), 2052-2056.
Battaglia and Ryan "Pathways of Polymeric Vesicle Formation," (2006) The Journal of Physical Chemistry B, 110, 102727-10279.
Battaglia and Ryan "The evolution of vesicles from bulk lamellar gels," (2005) Nat. Mater. 4, 869-876.
Battaglia et al. "Polymeric Vesicle Permeability: A Facile Chemical Assay," (2006), Lanmuir 22, 4910.
Battaglia et al. "Wet Nanoscale Imaging and Testing of Polymersomes," (2011) Small 7(14), 2010-2015.
Bieging et al. "Unravelling mechanisms of p53-mediated tumour suppression," (2014) Nat. Rev. Cancer 14, 359-370.
Blanazs et al. "Mechanistic Insights for Block Copolymer Morphologies: How Do Worms Form Vesicles?," (2011) J. Am. Chem. Soc. 133(41), 16581-16587.
Blanazs et al. "Tailoring Macromolecular Expression at Polymersome Surfaces," (2009) Adv. Funct. Mater. 19(18), 2906-2914.
Canton et al. "Fully synthetic polymer vesicles for intracellular delivery of antibodies in live cells," (2013) FASEB J. 27(1), 98-108.
Canton et al. "Scavenger receptors in homeostasis and immunity," (2013) Nature Rev. Imm. 13, 621-634.
Cecchin et al. "Enzyme-driven chemotactic synthetic vesicles", presented at 248th ACS National Meeting: Stimuli-responsive supramolecular, macromolecular and nanostructured systems and biopolymer-driven organization of nanostructures (2014).
Chambon et al. "Facile Synthesis of Methacrylic ABC Triblock Copolymer Vesicles by RAFT Aqueous Dispersion Polymerization," (2012) Macromolecules 45, 5081-5090.
Chambon et al. "How Does Cross-Linking Affect the Stability of Block Copolymer Vesicles in the Presence of Surfactant?," (2012) Langmuir 28, 1196-120.
Chen et al. "High-Purity Separation of Gold Nanoparticle Dimers and Trimers," (2009) Journal of the American Chemical Society 131, 4218-4219.
Christian et al. "Spotted vesicles, striped micelles and Janus assemblies induced by ligand binding" (2009) Nature Mater 8, 843-849.
Discher et al. "Polymersomes: Tough Vesicles Made from Diblock Copolymers," (1999) Science 284, 1143-1146.
Du et al. "pH-Sensitive Vesicles Based on a Biocompatible Zwitterionic Diblock Copolymer," (2005) J. Am. Chem. Soc 127(51), 17982-17983.
Ebbens et al. "Size dependence of the propulsion velocity for catalytic Janus-sphere swimmers," (2012) Phys. Rev. E 85 020401(R).
Gaitzsch et al. "Synthetic Bio-nanoreactor: Mechanical and Chemical Control of Polymersome Membrane Permeability," (2012) Angew. Chem. Int. Ed. 51, 4448-4451.
Gerold et al. "Locking out hepatitis C," (2011) Nature Medicine 17, 542-544.
Ghoreschi et al. "Fumarates improve psoriasis and multiple sclerosis by inducing type II dendritic cells," (2011) J Exp Med 208, 2291-2303.
Giacomelli et al. "Phosphorylcholine-Based pH-Responsive Diblock Copolymer Micelles as Drug Delivery Vehicles: Light Scattering, Electron Microscopy, and Fluorescence Experiments," (2006) Biomacromolecules 7, 817-828.
Gordon "Osmophoresis," (1981) J Phys. Chem. 85, 1753-1755.
Grumelard et al. "Soft nanotubes from amphiphilic ABA triblock macromonomers," (2004) Chemical Communications 13, 1462-1463.
Lee and Feihen "Polymersomes for drug delivery: Design, formation and characterization," (2012) J Control Release 161(2), 473-483.
Linker et al. "Fumaric acid esters exert neuroprotective effects in neuroinflammation via activation of the Nrf2 antioxidant pathway," (2011) Brain 134, 678-692.
Liu et al. "Hydrolysable core crosslinked particles for receptor-mediated pH-sensitive anticancer drug delivery" (2015) New Journal of Chemistry 39(11), 8840-8847.
Loewe et al. "Nuclear Entry of NF-kB/p65 in Human Dimethylfumarate Inhibits TNF-Induced Endothelial Cells," (2002) J. Immunol. 168, 4781-4787.
Lomas et al. "Biomimetic pH Sensitive Polymersomes for Efficient DNA Encapsulation and Delivery," (2007) Adv. Mater. 19, 4238-4242.
Lomas et al. "Efficient Encapsulation of Plasmid DNA in pHSensitive PMPC-PDPA Polymersomes: Study of the Effect of PDPA Block Length on Copolymer—DNA Binding Affinity," (2010) Macromolecular Bioscience 10, 513-530.
Lomas et al. "Non-cytotoxic polymer vesicles for rapid and efficient intracellular delivery," (2008) Faraday discussions 193, 143-159.
Lopresti et al. "Controlling Polymersome Surface Topology at the Nanoscale by Membrane Confined Polymer/Polymer Phase Separation," (2011) ACS NANO 5(3), 1775-1784.
Lopresti et al. "Polymersomes: nature inspired nanometer sized compartments," (2009) J. Mater. Chem. 19, 3576-3590.
Martín et al. "Template Electrosynthesis of High-Performance Graphene Microengines," (2015) Small 11(29), 3568-3574.
Massignani et al "Controlling Cellular Uptake by Surface Chemistry, Size, and Surface Topology at the Nanoscale," (2009) Small 5(21), 2424-2432.
Massignani et al "Enhanced Fluorescence Imaging of Live Cells by Effective Cytosolic Delivery of Probes," (2010) Plos One, 5(5): e10459.
Meng et al. "Stimuli-Responsive Polymersomes for Programmed Drug Delivery," (2009) Biomacromolecules 10(2), 197-209.
Murdoch et al. "Internalization and biodistribution of polymersomes into oral squamous cell carcinoma cells in vitro and in vivo," (2010) Nanomedicine 5, 1025-1036.
Najafi et al. "Biodegradable micelles/polymersomes from fumaric/sebacic acids and poly(ethylene glycol)," (2003) Biomaterials 24(7), 1175-1182.
Napoli et al., "Glucose-oxidase Based Self-Destructing Polymeric Vesicles," (2004) Langmuir 20(9), 3487-3491.
Neculai et al. "Structure of LIMP-2 provides functional insights with implications for SR-BI and CD36," (2013) Nature 504, 172-176.
Paul et al. "Ring-opening copolymerization (ROCOP): synthesis and properties of polyesters and polycarbonates," (2015) Chem. Commun. 51, 6459-6479.
Pearson et al. "Effect of pH and Temperature on PMPC-PDPA Copolymer Self-Assembly," (2013) Macromolecules 46, 1400-1407.
Reiner et al. "Optical manipulation of lipid and polymer nanotubes with optical tweezers," (2004) SPIE 5514, 246-253.
Reiner et al. "Stable and robust polymer nanotubes stretched from polymersomes," (2006) PNAS 103(5), 1173-1177.
Robertson et al. "pH-Sensitive Tubular Polymersomes: Formation and Applications in Cellular Delivery," (2014) ACS Nano 8(5), 4650-4661.
Robertson et al. "Purification of Nanoparticles by Size and Shape," (2016) Scientific Reports 6:27494.

(56) References Cited

OTHER PUBLICATIONS

Rosselgong et al. "Thiol-Functionalized Block Copolymer Vesicles," (2012) ACS Macro Letters 1, 1041-1045.
Ruiz-Perez et al. "Molecular engineering of polymersome surface topology," (2015) Sci Adv 2(4), e1500948).
Saha et al. "Clusters, asters, and collective oscillations in chemotactic colloids," (2014) Phys. Rev. E 89, 062316.
Sanchez-Lopez et al. "Evaluation of liposome populations using a sucrose density gradient centrifugation approach coupled to a continuous flow system," (2009) Analytica Chimica Acta 645, 79-85.
Scannevin et al. "Fumarates Promote Cytoprotection of Central Nervous System Cells against Oxidative Stress via the Nuclear Factor (Erythroid-Derived 2)—Like 2 Pathway," (2012) J, Pharmacol. Exp. Ther. 341, 274-284.
Sharma et al. "Nanocarriers as Promising Drug Vehicles for the Management of Tuberculosis," (2013) Bionanoscience 3(2), 102-111.
Steineweg et al. "Fast and Cost-Effective Purification of Gold Nanoparticles in the 20-250 nm Size Range by Continuous Density Gradient Centrifugation," (2011) Small 7(17), 2443-2448.
Sui et al. "Robust formation of biodegradable polymersomes by direct hydration," (2015) Polymer Chemistry 6(5), 691-696.
Sun et al. "Separation of Nanoparticles in a Density Gradient: FeCo@C and Gold Nanocrystals," (2008) Angewandte Chemie International Edition 48(5), 939-942.
Themistou et al. "Facile synthesis of thiol-functionalized amphiphilic polylactide-methacrylic diblock copolymers," (2014) Polymer Chem 5, 1405-1417.
Tian et al. "LRP-i.—mediated intracellular antibody delivery to the Central Nervous System," (2015) Scientific Reports 5:11990.
Van Oers et al. "Tubular Polymersomes: A Cross-Linker-Induced Shape Transformation," (2013) J. Am. Chem. Soc. 135(44), 16308-16311.
Vlieghe and Khrestchatisky "Peptide-based vectors for blood-brain barrier targeting and delivery of drugs to the central nervous system," (2010) Therapeutic Delivery 1(4), 489-494.
Wang et al. "Encapsulation of Biomacromolecules within Polymersomes by Electroporation," (2012) Angew. Chem., Int. Ed. 51, 11122-11125.
Yakovlev and Deming "Controlled Synthesis of Phosphorylcholine Derivatives of Poly(serine) and Poly(homoserine)," (2015) J. Am. Chem. Soc. 137(12), 4078-4081.
Yealland et al. "Rescue of mitochondrial function in parkin-mutant fibroblasts using drug loaded PMPC-PDPA polymersomes and tubular polymersomes," (2016) Neuroscience Letters 630, 23-29.
Yu et al. "Targeting Strategies for Multifunctional Nanoparticles in Cancer Imaging and Therapy," (2012) Theranostics 2(1), 3-44.
Chen, WC, GC Gompleto, DS Sigal, PR Crocker, A Seven, JC Paulson. "In vivo targeting of B-cell lymphoma with glycan ligands of CD22." Blood, vol. 115, No. 23, Jun. 2010, pp. 4778-4786.
Joseph, A. et al. "Chemotactic synthetic vesicles: Design and applications in blood-brain barrier crossing." Science Advances, vol. 3, 2017, item e1700362, pp. 1-12, published Aug. 2, 2017.
Kim, KT, JJLM Cornelissen, RJM Nolte, JCM van Hest. "A Polymersome Nanoreactor with Controllable Permeability Induced by Stimuli-Responsive Block Copolymers." Advanced Materials, vol. 21, 2009, pp. 2787-2791.
Lagzi. I. "Chemical robotics—chemotactic drug carriers." Central European Journal of Medicine, vol. 8(4), 2013, pp. 377-382.
Peng, F., Y Tu, JCM van Hest, DA Wilson. "Self-Guided Supramolecular Cargo-Loaded Nanomotors with Chemotactic Behavior towards Cells." Angewandte Communications International Edition, vol. 54, 2015, pp. 11662-11665.
Sahari, A., MA Traore, BE Scharf, B Behkam. "Directed transport of bacteria-based drug delivery vehicles: bacterial chemotaxis dominates particle shape." Biomedical Microdevices, vol. 16 Issue 5, 2014, pp. 717-725.
Georgieva, Julia V et al., "Peptide-Mediated Blood-Brain Barrier Transport of Polymersomes," Angewandte Chemie International Edition, 2012, 51, 8339-8342.
Pulicherla, K. K. and Mahendra Kumar Verma, "Targeting Therapeutics Across the Blood Brain Barrier (BBB), Prerequisite Towards Thrombolytic Therapy for Cerebrovascular Disorders—an Overview and Advancements," AAPS PharmSciTech, vol. 16, No. 2, Apr. 2015, pp. 223-233.

* cited by examiner

FUMARATE POLYMERSOMES

CROSS-REFERENCE TO RELATED APPLICATIONS

This application is a national stage application under 35 U.S.C. § 371 of International Patent Application No. PCT/GB2017/050756, filed Mar. 17, 2017, which claims priority to GB Application No. 1604553.6, filed Mar. 17, 2016, the disclosures both of which are hereby incorporated by reference for all purposes in their entireties.

FIELD OF THE INVENTION

The present invention relates to fumarate polymersomes. The polymersomes are capable of targeting immune cells and then hydrolysing to release the immunomodulatory compound fumarate. The polymersomes can thus be used in methods for the treatment and/or prevention of diseases, including immune diseases (including autoimmune diseases) such as multiple sclerosis, arthritis, psoriasis and other disorders involving inflammation (such as stroke and neurodegenerative conditions).

BACKGROUND OF THE INVENTION

A vast range of human and animal diseases are associated with inflammatory abnormalities. For example, a wide range of immune disorders are associated with abnormal inflammation. Furthermore, a number of non-immune diseases are associated with inflammatory processes, including cancer, atherosclerosis, stroke, and ischemic heart disease.

Fumarate is a critical component of the Krebs cycle. It has been proven to act as immunomodulator and demonstrated to have helpful effects in several preclinical models of oxidative stress, neuroinflammation, and neurodegeneration. Although the mechanism of action of fumarates has not been completely established, there is evidence that it involves the activation of the nuclear 1 factor (erythroid-derived 2)-like 2 (Nrf2) antioxidant response pathway, which is the primary cellular defense against the oxidative stress. Another proposed effect of fumarate is the modulation of immune cell responses through the prevention of proinflammatory-cytokine production, the inhibition of pro-inflammatory pathways and the shifting of dendritic-cell differentiation.

Fumarate esters have already been approved for the treatment of psoriasis and multiple sclerosis. Fumarate esters are also under clinical evaluation for enhancing cancer chemotherapy and radiotherapy (more specifically, in the treatment of glioblastoma multiforme) and for the treatment of psoriatic arthritis, lupus erythematosus, rheumatoid arthritis, cutaneous T-cell lymphoma and obstructive sleep apnea. Still further, it has been reported that fumarates may be effective for limiting the progression of HIV and reducing inflammation as well as being proposed for the treatment of stroke and Alzheimer's disease. Fumarate is also a common solubilising agent used for formulating several drugs (including bisoprolol fumarate, Quetiapine Fumarate, Disoproxil Fumarate and ferrous fumarate).

Currently approved fumarate medicaments are formulated as pills for oral administration. As with many orally formulated medicaments, the delivery of active agent by systemic means and in an untargeted manner has been observed to give rise to significant deleterious side effects. It would be desirable to provide medicaments that more effectively deliver the therapeutic agent to loci of interest, thus enabling the same or a better therapeutic result to be achieved when using a lower dosing amount, and/or the reduction of side effect profiles. The present invention addresses these issues and provides improved medicaments for the therapeutic delivery of fumarate.

SUMMARY OF THE INVENTION

The present invention addresses these problems via the provision of a polymersome that comprises: (a) a phosphorylcholine polymer; and (b) a fumarate polymer.

Polymersomes (vesicles formed from amphiphilic block copolymers) are the polymeric equivalent of liposomes. They are known to be much more robust and stable than their lipid counterparts due to their macromolecular nature. In addition, their macromolecular nature also allows a very effective tuning of the membrane thickness. Polymersomes that are sensitive to pH have previously been developed and shown to be capable of delivering certain types of molecules to the cell cytosol.

It has now been found that polymersomes comprising the components (a) and (b) provide a highly selective and efficient means of treating diseases. In particular, diseases that can be treated using the polymersomes of the invention include any disease that is susceptible to treatment or prevention by fumarate. Notable examples of such diseases are inflammatory disorders, including immune disorders and non-immune diseases as further defined herein.

It has been found that the components (a) and (b) within the polymersomes function synergistically. The component (a) selectively targets scavenger receptor B1 over-expressed by macrophages and other immune cells. The component (b) releases the active agent fumarate by in situ hydrolysis. The capacity of the polymersomes of the invention significantly to decrease the expression level of inflammatory cytokines has been proven experimentally.

The present invention additionally provides a pharmaceutical composition comprising: a plurality of the polymersomes of the present invention; and one or more pharmaceutically acceptable excipients or diluents.

Still further, the present invention provides the polymersome of the present invention, for use as a medicament. The present invention also provide the polymersome of the present invention, for use in a method for the treatment or prevention of an inflammatory disorder. The present invention additionally provides the polymersome of the present invention, for use in a method for the treatment or prevention of multiple sclerosis, psoriatic arthritis, rheumatoid arthritis, lupus erythematosus, psoriasis, cancer and obstructive sleep apnoea. Furthermore, the present invention provides a method of treating or preventing multiple sclerosis, psoriatic arthritis, rheumatoid arthritis, lupus erythematosus, psoriasis, cancer and obstructive sleep apnoea in a subject in need thereof, the method comprising administering a therapeutically effective amount of the polymersome of the present invention to the subject. Still further, the present invention provides use of a polymersome of the present invention in the manufacture of a medicament for use in the treatment or prevention of multiple sclerosis, psoriatic arthritis, rheumatoid arthritis, lupus erythematosus, psoriasis, cancer and obstructive sleep apnoea.

DETAILED DESCRIPTION OF THE INVENTION

Polymersome

Figure 1:
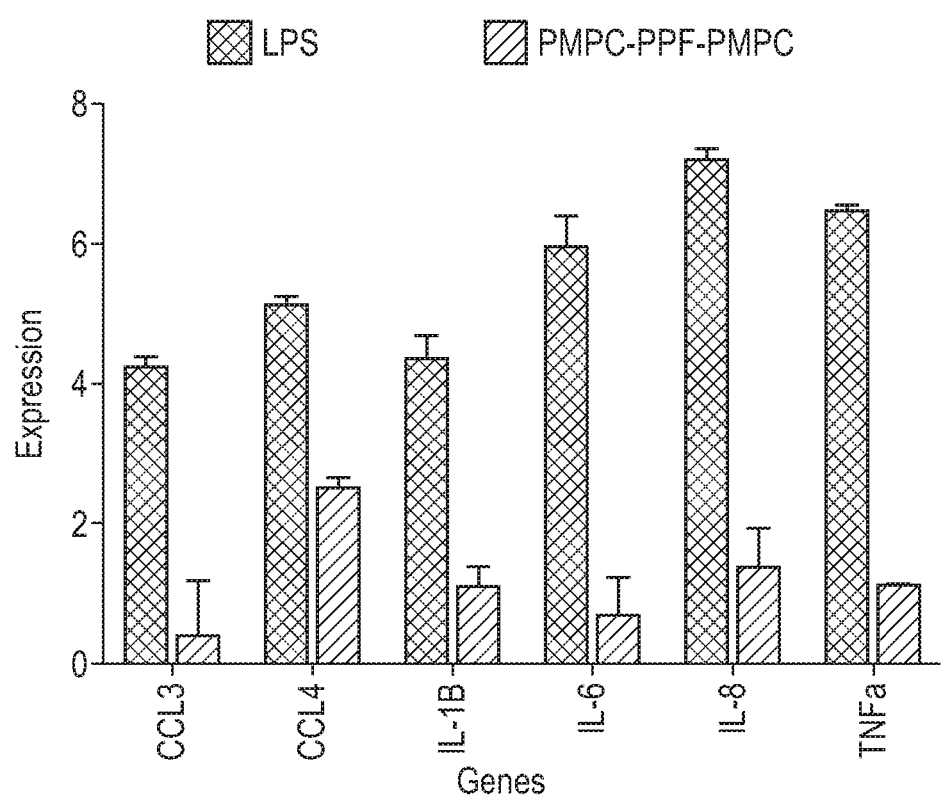
FIG. 1 shows the expression levels of cytokines in cells exposed to the fumarate polymersome as described in Example 1.

Polymersomes are synthetic vesicles formed from amphiphilic block copolymers. Over the last fifteen years they have attracted significant research attention as versatile carriers because of their colloidal stability, tuneable membrane properties and ability in encapsulating or integrating other molecules (for one representative review article, see *J Control Release* 2012 161(2) 473-83, the contents of which are herein incorporated by reference in their entirety).

The polymersome used in the present invention is typically a self-assembled structure. The polymersome typically comprises an amphiphilic block copolymer. An amphiphilic block copolymer comprises a hydrophilic block and a hydrophobic block. In the polymersomes of the present invention typically the hydrophilic block comprises the phosphorylcholine polymer (a) and the hydrophobic block comprises the fumarate polymer (b).

Such polymersomes are able to mimic biological phospholipids. Molecular weights of these polymers are much higher than naturally-occurring phospholipid-based surfactants such that they can assemble into more entangled membranes (*J. Am. Chem. Soc.* 2005, 127, 8757, the contents of which are herein incorporated by reference in their entirety), providing a final structure with improved mechanical properties and colloidal stability. Furthermore, the flexible nature of the copolymer synthesis allows the application of different compositions and functionalities over a wide range of molecular weights and consequently of membrane thicknesses. Thus the use of these block copolymers as delivery vehicles offers significant advantages.

Polymersomes are often substantially spherical. Polymersomes typically comprise a bilayered membrane. The bilayer is generally formed from two layers of amphiphilic molecules, which align to form an enclosed core with hydrophilic head groups facing the core and the exterior of the vesicle, and hydrophilic tail groups forming the interior of the membrane.

A typical (largest) diameter of a polymersome is in the range 50 to 5000 nm. More typically, the diameter is in the range 50 to 1000 nm. Polymersomes having a diameter in this range are normally termed "nanopolymersomes" or "nanovesicles". The nanopolymersomes are preferably substantially spherical in shape. Typically, the nanopolymersomes have a number average diameter of less than 300 nm, preferably less than 250 nm, most preferably less than 200 nm or 150 nm. The thickness of the bilayer is generally between 2 to 50 nm, more typically between 5 and 20 nm. These dimensions can routinely be measured, for example by using Transmission Electron Microscopy (TEM) and/or and Small Angle X-ray Scattering (SAXS) (see, for example, *J. Am. Chem. Soc.* 127 8757 2005, the contents of which are herein incorporated by reference in their entirety).

In aqueous solution, normally an equilibrium exists between different types of structures, for instance between polymersomes and micelles. It is preferred that at least 80%, more preferably at least 90% or 95% by weight and most preferably all of the structures in solution are present as polymersomes. This can be achieved using the methods outlined herein.

The polymersome is capable of releasing fumarate in vivo after administration to a subject. Typically the polymersome dissociates and the fumarate is released as a result of hydrolysis of the fumarate polymer. The fumarate polymer is thus a polymer whose hydrolysis releases fumarate.

If the polymersome comprises a drug encapsulated within the polymersome then the polymersome is also capable of releasing the drug in vivo after administration to a subject. Again, typically the polymersome dissociates and drug is thereby released.

As explained already, component (a) of the polymersome selectively targets scavenger receptor B1 highly expressed by macrophages and other immune cells; in particular it enables the polymersome to enter such cells. Release of fumarate (and encapsulated drug, if any) may thus typically occur, at least in part, after the polymersome has been internalised within an immune cell. However, the present invention also provides for release of fumarate (and encapsulated drug, if any) in the vicinity of an immune cell (i.e. a targeted immune cell).

Dissociation of the polymersome may be promoted by a variety of mechanisms, but is often promoted by the hydrolysis of the hydrophobic block copolymer. Specifically, the ester bonds in the fumarate are hydrolysed releasing fumarate. This process is catalysed by enzymes known as esterases and by acidic pH. Both conditions are typical of endo-lysosome compartments where the polymersomes traffic to upon endocytosis.

Typically, the phosphorylcholine polymer (a) carries a phosphorylcholine group (typically as a pendant group), which typically has a pKa in the range 3.0 to 6.9. The process of endocytosis includes a reduction in the local pH experienced by the polymersome from around pH 7.4 to around pH 5-6. This pH drop is typically sufficient to trigger disintegration of the polymersome.

pKa means the pH where half of the pendant groups are ionised. pKa can be determined by a variety of methods including pH titration followed by potentiometric titration, UV spectroscopy and Dynamic Light Scattering (DLS). An appropriate method should be selected to measure the pKa according to the copolymer which is being analysed and its solubility in the test media.

DLS is a particularly preferred method for measuring pKa. As indicated in *J. Am. Chem. Soc* 2005 127 17982-17983, the contents of which are herein incorporated by reference in their entirety, the DLS signal from a copolymer, such as $PMPC_{25}$-b-$PDPA_{20}$ copolymer, in water varies with pH. At a certain pH the signal rapidly increases as the copolymer undergoes a transition from being molecularly deassociated to associated. The pKa is taken as the pH of the mid-point of this rapid increase. These experiments are described further in Biomacromolecules 2006, 7, 817-828, the contents of which are herein incorporated by reference in their entirety. In this reference, the experiments are performed on micelles of block copolymer, but the techniques may also be applied when the phase transition involves polymersome formation.

The pKa of a group in a polymer is determined on the basis of a polymer system (and not assumed to be the same as the pKas of similar moieties in non-polymeric systems).

The fumarate polymer (b) of the polymersome may also comprise pendant cationisable moieties as pendant groups. Cationisable moieties are, for instance, primary, secondary or tertiary amines, capable of being protonated at pHs below a value in the range 3 to 6.9. Alternatively the group may be a phosphine.

Preferably, the pKa of the pendant groups is in the range 4.0 to 6.9, more preferably 5.5 to 6.9. The polymersomes are correspondingly capable of disassociating in such pH ranges.

Preferably, the fumarate polymer (b) (the hydrophobic block of the polymersome) has a degree of polymerisation of at least 50, more preferably at least 70. Preferably, the degree of polymerisation is no more than 250, even more preferably, no more than 200. Typically, the degree of polymerisation is at least 15, more preferably at least 20.

It is preferred that the ratio of the degree of polymerisation of the phosphorylcholine polymer (a) (the hydrophilic block) to the fumarate polymer (b) (the hydrophobic block) is in the range 1:2.5 to 1:8. All of these limitations promote polymersome, rather than micelle formation.

The phosphorylcholine polymer (a) may be based on condensation polymers, such as polyesters, polycarbonates, polyamides, polyanhydrides, polyurethanes, polyethers (including polyalkylene glycols, especially PEG), polyimines, polypeptides, polyureas, polyacetals and polysaccharides, but preferably is based on a radical polymerised addition polymer of ethylenically unsaturated monomers. The phosphorylcholine polymer may comprise phosphorylcholine as pendant groups, in which case the pendant groups may be present in the monomers and remain unchanged in the polymerisation process. It is alternatively possible to derivatise the pendant group of a monomer to transform it into a phosphorylcholine group after polymerisation.

In one currently preferred embodiment, the phosphorylcholine polymer (a) is formed from ethylenically unsaturated monomers. Non-limiting suitable ethylenically unsaturated monomers have the general formula (IV)

$$YBX \quad (IV),$$

in which:

Y is an ethylenically unsaturated group selected from $H_2C=CR-CO-A-$, $H_2C=CR-C_6H_4-A^1-$, $H_2C=CR-CH_2-A^2-$, $R^2O-CO-CR=CR-CO-O-$, $RCH=CH-CO-O-$, $RCH=C(COOR^2)CH_2-CO-O-$, and A is —O— or $NR^1$;
$A^1$ is selected from a bond, $(CH_2)_LA^2$ and $(CH_2)_LSO_3^-$ in which L is 1 to 12;
$A^2$ is selected from a bond, —O—, —O—CO—, —CO—O, —CO—$NR^1$—, —$NR^1$—CO—, —O—CO—$NR^1$— and —$NR^1$—CO—O—;
R is hydrogen or $C_{1-4}$ alkyl;
$R^1$ is hydrogen, $C_{1-4}$ alkyl or BX;
$R^2$ is hydrogen or $C_{1-4}$ alkyl;
B is a bond, or a straight or branched alkanediyl, alkylene oxaalkylene, or alkylene (oligooxalkylene) group, optionally containing one or more fluorine substituents; and X is a phosphorylcholine group, i.e. a group having the formula In the monomer of the general formula (IV) it is preferred that the ethylenic unsaturated group Y is $H_2C=CR-CO-A-$. Such acrylic moieties are preferably methacrylic, that is in which R is methyl, or acrylic, in which R is hydrogen. Whilst the compounds may be (meth)acrylamido compounds (in which A is $NR^1$), in which case $R^1$ is preferably hydrogen, or less preferably, methyl, most preferably the compounds are esters, that is in which A is O.

In monomers of the general formula (IV), especially where Y is the preferred (alk)acrylic group, B is most preferably an alkanediyl group. Whilst some of the hydrogen atoms of such group may be substituted by fluorine atoms, preferably B is an unsubstituted alkanediyl group, most preferably a straight chain group having 2 to 6 carbon atoms.

A particularly preferred monomer of general formula (IV) is 2-methacryloyloxyethyl-phosphorylcholine (MPC). Mixtures of monomers each having the above general formula may be used, as can mixtures with other monomers, e.g. with other hydrophilic monomers.

Preferably, the phosphorylcholine polymer (a) is an acrylate polymer. An acrylate polymer is a polymer formed from one or more acrylate monomers. An acrylate monomer is a monomer comprising an acrylate group (i.e. $CH_2=CH-COO-$) which may be substituted or unsubstituted and as such includes methacrylate monomers and other such monomers covered by formula (IV). Preferably, the phosphorylcholine polymer (a) is a polymer that comprises pendant phosphorylcholine groups. Particularly preferably, the phosphorylcholine polymer (a) is an acrylate polymer that comprises pendant phosphorylcholine groups. For example, the phosphorylcholine polymer (a) may comprise units of formula (I)

(I)

in which $R^p$ is hydrogen or methyl and $A^p$ is a group of formula (I')

(I')

in which $X^p$ is a $C_{1-6}$ alkylene group. In some cases, $X^p$ may be one or more amino acids, for instance an oligoamino acid or a polyamino acid. An oligoamino acid may comprise from 1 to 300 amino acids, for instance from 1 to 50 aminor acids. Typically, an oligoamino acid comprises from 4 to 50 amino acids.

Preferably $X^p$ is a $C_2$-6 alkylene group. Preferably $R^p$ is methyl. In a particularly preferred embodiment the phosphorylcholine polymer is poly(2-methacryloyloxy ethyl phosphorylcholine).

Alternatively, the phosphorylcholine polymer (a) may be a polypeptide, for instance those described in Yakovlev and Deming, *J. Am. Chem. Soc.*, 2015, 137 (12), pp 4078-4081 the entirety of which is incorporated by reference. For instance, the phosphorylcholine polymer (a) may comprise poly(L-phosphorylcholine serine) or poly(L-phosphorylcholine homoserine).

The fumarate polymer (b) is a typically a polymer that comprises a fumarate unit of formula (II)

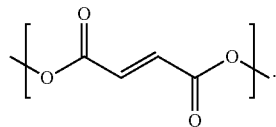

(II)

Typically the polymer (b) comprises a plurality of such fumarate units.

Degradation, e.g. hydrolysis, of the fumarate polymer (b) generates fumarate. Thus the fumarate polymer is typically susceptible to degradation, e.g. hydrolysis, in vivo, for example following endocytosis (e.g., into an immune cell such as a macrophage).

The fumarate polymer (b) may comprise pendant groups that comprise the fumarate unit of formula (II), in which case the pendant groups are susceptible to degradation to release fumarate. Typically, however, the fumarate polymer comprises fumarate units of formula (II) within its skeleton (optionally with additional pendant groups that comprise the fumarate units).

For example, the fumarate polymer may comprise repeating units of formula (III)

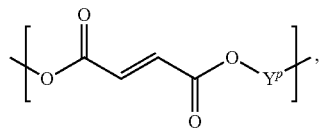

(III)

wherein $Y^p$ is a straight chain or branched $C_{1-6}$ alkylene group. Particularly preferred repeating units of formula (III) are those where $Y^p$ is —CH(CH$_3$)CH$_2$—.

A particularly preferred fumarate polymer is poly(propylene fumarate). An advantage of this fumarate polymer is that the secondary product of its hydrolysis is propylene glycol which is generally recognised as safe material and already approved for several clinical applications. Propylene glycol is metabolized by the liver to form lactate, acetate, and pyruvate. The non-metabolised drug is excreted in the urine mainly as the glucuronide conjugate, approximately 12 to 45 percent is excreted unchanged in urine.

The fumarate polymer may also be a copolymer. For example, the fumarate polymer may comprise fumarate units of formula (II) and/or repeating units of formula (III), together with repeating units derived from other monomers. Suitable monomers include monomers known in the art for forming the hydrophobic block of polymersomes.

Non-limiting examples of such monomers include those having the general formula (V)

$$Y^1 B^1 Q \qquad (V),$$

in which $Y^1$ is selected from $H_2C=CR^{14}$—CO-$A^8$-, $H_2C=CR^{14}$—$C_6H_4$-$A^9$-, $H_2C=CR^{14}$—$CH_2A^{10}$-, $R^{16}O$—CO—$CR^{14}=CR^{14}$—CO—O—, $R^{14}CH=CH$—CO—O—, $R^{14}CH=C(COOR^{16})CH_2$—CO—O—,

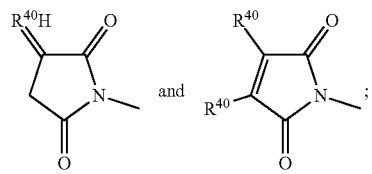

$A^8$ is —O— or —NR$^{15}$—;
$A^9$ is selected from a bond, $(CH_2)_q A_{10}$ and $(CH_2)_q SO_3^-$ in which q is 1 to 12;
$A^{10}$ is selected from a bond, —O—, —O—CO—, —CO—O—, —CO—NR$^{15}$—, —NR$^{15}$—CO—, —O—CO—NR$^{15}$—, —NR$^{15}$—CO—O—;
$R^{14}$ is hydrogen or $C_{1-4}$ alkyl;
$R^{15}$ is hydrogen, $C_{1-4}$ alkyl or $B^1Q$;
$R^{16}$ is hydrogen or $C_{1-4}$ alkyl;
$B^1$ is a bond, or a straight or branched alkanediyl, alkylene oxaalkylene, or alkylene (oligooxalkylene) group, optionally containing one or more fluorine substituents; and
Q is a cationic or cationisable group of the formula —NR$^{17}_p$, —PR$^{17}_p$ and SR$^{17}_r$, in which p is 2 or 3, r is 1 or 2, the groups $R^{17}$ are the same or different and each is selected from the group consisting of hydrogen, $C_{1-24}$ alkyl and aryl, or two of the groups $R^{17}$ together with the heteroatom to which they are attached from a 5 to 7 membered heterocyclic ring or three $R^{17}$ groups together with the heteroatom to which they are attached form a 5 to 7 membered heteroaromatic ring, either of which rings may be fused to another 5 to 7 membered saturated or unsaturated ring, and any of the $R^{17}$ groups may be substituted by amino or hydroxyl groups or halogen atoms; wherein if p is 3, at least one of the groups $R^{17}$ is hydrogen.

Preferably $Y^1$ is $H_2C=CR^{14}$—CO-$A^8$- where $R^{14}$ is H or methyl and $A^8$ is O or NH. Preferred groups $B^1$ are alkanediyl, usually with linear alkyl chains and preferably having 2 to 12 carbon atoms, such as 2 or 3 carbon atoms.

Preferably Q is NR$^{17}_2$ where $R^{17}$ is $C_{1-12}$-alkyl. Preferably both $R^{17}$s are the same. Particularly useful results have been achieved where the groups $R^{17}$ are $C_{1-4}$ alkyl, especially ethyl, methyl or isopropyl.

More generally, either or both the polymers (a) and (b) may include comonomers, for instance to provide functionality, control over hydrophobicity, control over pH sensitivity, pKa or pKb as the case may be, control over temperature sensitivity or as general diluents. For instance comonomers providing functionality may be useful to provide conjugation of pendant groups following polymerisation and/or polymersome formation, to provide targeting moieties, or to provide for conjugation between the biologically active molecule and the polymer. Alternatively, functional groups may allow for crosslinking of the polymer following polymersome formation, to confer increased stability on the polymersome structure. Examples of suitable comonomers are compounds of the general formula (VI)

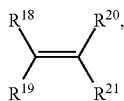

(VI)

in which

R[18] is selected from hydrogen, halogen, $C_{1-4}$ alkyl and groups COOR[22] in which R[22] is hydrogen or $C_{1-4}$ alkyl;

R[19] is selected from hydrogen, halogen and $C_{1-4}$ alkyl;

R[20] is selected from hydrogen, halogen, $C_{1-4}$ alkyl and groups COOR[22] provided that R[18] and R[20] are not both COOR[22]; and R[21] is a $C_{1-10}$ alkyl, a $C_{1-20}$ alkoxycarbonyl, a mono- or di-($C_{1-10}$ alkyl)amino carbonyl, a $C_{6-20}$ aryl (including alkaryl) a $C_{7-20}$ aralkyl, a $C_{6-20}$ aryloxycarbonyl, a $C_{1-20}$-aralkyloxycarbonyl, a $C_{6-20}$ arylamino carbonyl, a $C_{7-20}$ aralkyl-amino, a hydroxyl or a $C_{2-10}$ acyloxy group, any of which may have one or more substituents selected from halogen atoms, alkoxy, oligo-alkoxy, aryloxy, acyloxy, acylamino, amine (including mono and di-alkyl amino and thalkylammonium in which the alkyl groups may be substituted), carboxyl, sulphonyl, phosphoryl, phosphino, (including mono- and di-alkyl phosphine and tri-alkylphosphonium), zwitterionic, hydroxyl groups, vinyloxycarbonyl and other vinylic or allylic substituents, and reactive silyl or silyloxy groups, such as trialkoxysilyl groups; or R[21] and R[20] or R[21] and R[19] may together form —CONR[23]CO in which R[23] is a $C_{1-20}$ alkyl group.

It is preferred for at least two of the groups R[18], R[19], R[20] and R[21] to be halogen or, more preferably, hydrogen atoms. Preferably R[18] and R[19] are both hydrogen atoms. It is particularly preferred that compound of general formula X is a styrene or acrylic compound. In styrene compounds R[21] represents an aryl group, especially a substituted aryl group in which the substituent is an amino alkyl group, a carboxylate or a sulphonate group. Where the comonomer is an acrylic type compound, R[21] is an alkoxycarbonyl, an alkyl amino carbonyl, or an aryloxy carbonyl group. Most preferably in such compounds R[21] is a $C_{1-20}$-alkoxy carbonyl group, optionally having a hydroxy substituent. Acrylic compounds are generally methacrylic in which case R[20] is methyl.

Preferably the comonomer is a non-ionic comonomer, such as a $C_{1-24}$ alkyl(alk)-acrylate or -acrylamide, mono- or di-hydroxy-$C_{1-6}$-alkyl(alk)-acrylate, or acrylamide, oligo ($C_{2-3}$ alkoxy) $C_{2-18}$-alkyl (alk)-acrylate, or -acrylamide, styrene, vinylacetate or N-vinyllactam.

For optimum nanovesicle formation, the block copolymers should have controlled molecular weights. It is preferable for each of the blocks to have molecular weight controlled within a narrow band, that is, to have a narrow polydispersity. The polydispersity of molecular weight should, for instance, be preferably less than 2.0, more preferably less than 1.5, for instance in the range 1.1 to 1.4.

In one particularly preferred embodiment of this invention, the polymersome comprises poly(2-methacryloyloxy) ethyl phosphorylcholine and poly(propylene fumarate). In this particularly preferred embodiment, the polymersome typically comprises a block copolymer in which one block comprises poly(2-methacryloyloxy)ethyl phosphorylcholine and another block comprises poly(propylene fumarate). In an exemplary embodiment the polymersome comprises a block copolymer comprising a poly(2-methacryloyloxy) ethyl phosphorylcholine block and a poly(propylene fumarate) block.

The block copolymer may be a simple A-B block copolymer, or may be an A-B-A or B-A-B block linear triblock copolymer or a (A)$_2$B or A(B)$_2$ star copolymer (where A is the phosphorylcholine polymer containing block and B is the fumarate polymer containing block). It may also be an A-B-C, A-C-B or B-A-C linear triblock copolymers or an ABC star copolymer, where C is a different type of block. C blocks may, for instance, comprise functional, e.g. cross-linking or ionic groups, to allow for reactions of the copolymer, for instance in the novel compositions. Crosslinking reactions especially of A-C-B type copolymers, may confer useful stability on polymersomes. Cross-linking may be covalent, or sometimes, electrostatic in nature. Cross-linking may involve addition of a separate reagent to link functional groups, such as using a difunctional alkylating agent to link two amino groups. The block copolymer may alternatively be a star type molecule with hydrophilic or hydrophobic core, or may be a comb polymer having a hydrophilic backbone (block) and hydrophobic pendant blocks or vice versa. Such polymers may be formed for instance by the random copolymerisation of monounsaturated macromers and monomers.

In some cases, the phosphorylcholine polymer (a) may be coupled with a polymer (i.e. a C block) synthesised from epoxides, anhydrides, lactides and/or $CO_2$ to produce polyesters and polycarbonates. Examples of such polymers are those described in Shyeni and Williams, *Chem. Commun.*, 2015, 51, 6459, the entirety of which is incorporated by reference.

Further details of a suitable process for polymerising the monomers are to be found in WO 03/074090, the contents of which are herein incorporated by reference in their entirety.

The methods to be used for polymerising the monomers are living radical polymerisation process, functional NCA (N-carboxyanhydride) polymerisation with efficient postpolymerization modification and ring opening polymerisation (ROP). Living radical polymerisation has been found to provide polymers of monomers having a polydispersity (of molecular weight) of less than 1.5, as judged by gel permeation chromatography. Polydispersities in the range 1.2 to 1.4 for the or each block are preferred. The polymersomes may be loaded using a pH change system, electroporation or film hydration. In a pH change system process, polymer is dispersed in aqueous liquid in ionised form, in which it solubilises at relatively high concentrations without forming polymersomes. Subsequently the pH is changed such that some or all of the ionised groups become deprotonated so that they are in non-ionic form. At the second pH, the hydrophobicity of the block increases and polymersomes are formed spontaneously.

A method of forming polymersomes with a drug encapsulated in the core may involve the following steps: (i) dispersing the amphiphilic copolymer in an aqueous medium; (ii) acidifying the composition formed in step (i); (iii) adding the drug to the acidified composition; and (iv) raising the pH to around neutral to encapsulate the drug.

This method preferably comprises a preliminary step wherein the amphiphilic copolymer is dispersed in an organic solvent in a reaction vessel and the solvent is then evaporated to form a film on the inside of the reaction vessel.

Step (ii), of acidifying the composition, typically reduces the pH to a value below the pKa of the phosphorylcholine group.

Another method of forming polymersomes with a drug encapsulated in the core may involve the following steps: (i) dispersing the amphiphilic copolymer, and when needed the hydrophobic and/or amphiphilic drug, in an organic solvent in a reaction vessel; (ii) evaporating the solvent to form a film on the inside of the reaction vessel; and (iii) re-hydrating the film with an aqueous solution, optionally comprising a solumbilised hydrophilic drug.

In more detail, polymersomes are typically prepared by dissolving copolymer in an organic solvent, such as a 2:1 chloroform:methanol mix in a glass container. If a hydrophobic or amphiphilic drug is to be encapsulated, it can be added with the copolymer. Solvent can be evaporated under vacuum leaving a copolymeric film deposited on the walls of the container. The film is then re-hydrated with an aqueous solution, for instance using phosphate buffer saline. If a hydrophilic drug is to be encapsulated, it can be included in the aqueous solution. The pH of the resultant suspension is decreased to a pH of around 2, to solubilise the film, and then increased slowly to a pH or around 6. The polymer hydration at neutral pH allows the encapsulation of the drug. The dispersion may then be sonicated and extruded, for instance using a bench top extruder. UV spectroscopy and HPLC chromatography may be used to calculate the encapsulation efficiency, using techniques well known in the art. An alternative method for forming polymersomes with an encapsulated drug may involve simple electroporation of the drug and polymer vesicles in water. For instance the drug may be contacted in solid form with an aqueous dispersion of polymer vesicles and an electric field applied to allow the formation of pores on the polymersomes membrane. The solubilised drug molecules may then enter the polymersome vesicles though the pores. This is followed by membrane self healing process with the consecutive entrapment of the active molecules inside the polymersomes.

Alternatively, drug dissolved in organic solvent may be emulsified into an aqueous dispersion of polymer vesicles, whereby solvent and drug become incorporated into the core of the vesicles, followed by evaporation of solvent from the system.

The polymersomes used in the invention may be formed from two or more different block copolymers. In this embodiment, in the method of forming polymersomes, a mixture of the two or more block copolymers is used.

For example, 0.01% to 10% (w/w) of drug is mixed with copolymer in the methods described above.

Encapsulated Drug

The polymersome of the invention may comprise a drug encapsulated within the polymersome.

It will be understood that the polymersome of the invention is a therapeutically active substance per se, in view of its capacity to release fumarate in vivo. Nonetheless, it may be useful to provide a further drug encapsulated within the polymersome. For the avoidance of doubt it is also possible to encapsulate a plurality of different drugs within a single polymersome, or to provide a plurality of polymersomes each containing a particular encapsulated drug.

Examples of suitable drugs include drugs known for the treatment of inflammation, immune diseases (e.g. multiple sclerosis, psoriatic arthritis, rheumatoid arthritis, lupus erythematosus and psoriasis), cancer, obstructive sleep apnoea and HIV. Immunomodulatory drugs ("immunomodulators") are one preferred class of drugs. Drugs may also include NSAIDs, corticosteroids, DMARDs, immunosuppressants, TNF-alpha inhibitors and anti-cancer compounds.

Examples of anti-cancer compounds include cytotoxins. Non-limiting examples of specific cytotoxins include Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vemurafenib, Vinblastine, Vincristine, Vindesine and Vinorelbine. Polymersomes encapsulating an anti-cancer compound are of course particularly suited for use in methods for the treatment of cancer, such as the cancers discussed elsewhere herein.

Non-limiting examples of specific drugs that may be encapsulated include carnosine, asiatic acid, flavonoids (e.g. xanthohumol, naringenin, galangin, fisetin and baicalin), cannabinoids (e.g., WIN55,212-2, JWH-133 and TAK-937), citicoline, minocycline, cerebrolysin, ginsenosoid-Rd, granulocyte-colony stimulating factor, Tat-NR2B9c, magnesium, albumin, paracetamol, aspirin, choline and magnesium salicylates, celecoxib, diclofenac (e.g. diclofenac potassium, diclofenac sodium), diflunisal, etodolac, fenoprofen, flurbiprofen, ibuprofen, indomethacin, ketoprofen, meclofenamate, mefenamic acid, meloxicam, nabumetone, naproxen (including naproxen sodium), oxaprozin, piroxicam, rofecoxib, salsalate, sodium salicylate, sulindac, tolmetin, valdecoxib, corticosteroids, alemtuzumab, interferon beta-1b, fingolimod, glatiramer acetate, natalizumab, plegridy, peginterferon beta 1a, teriflunomide, methotrexate, sulfasalazine, leflunomide, adalimumab, etanercept, golimumab, ustekinumab, azathioprine, cyclosporine, infliximab, golimumab, certolizumab, hydroxychloroquine, methotrexate, azathioprine, mycophenolate, acitretin, hydrea, isotretinoin, mycophenolate mofetil, sulfasalazine, 6-thioguanine, calcipotriol, calcitriol, tacalcitol, tacrolimus, pimecrolimus, dithranol, endamustine, bendamustine, carmustine, chlorambucil, cyclophosphamide, dacarbazine, ifosfamide, melphalan, procarbazine, streptozocin, temozolomide, capecitabine, 5-Fluoro Uracil, Fludarabine, Gemcitabin, Methotrexate, Pemetrexed, Raltitrexed, Actinomycin D, Bleomycin, Doxorubicin, Epirubicin, Mitomycin, Mitoxantrone, Etoposide, Docetaxel, Irinotecan, Paclitaxel, Topotecan, Vinblastine, Vincristine, Vinorelbine, Eribulin, Carboplatin, Cisplatin, Oxaliplatin, Afatinib, Aflibercept, BCG, Bevacizumab, Brentuximab, Cetuximab, Crizotinib, Denosumab, Erlotinib, Gefitinib, Imatinib, Interferon, Ipilimumab, Lapatinib, Panitumumab, Pertuzumab, Rituximab, Sunitinib, Sorafenib, Trastuzumab emtansine, Temsirolimus, Trastuzumab, Vemurafenib, Clodronate, Ibandronic acid, Pamidronate, Zolendronic acid, Anastrozole, Abiraterone, Bexarotene, Bicalutamide, Buserelin, Cyproterone, Degarelix, Exemestane, Flutamide, Folinic acid, Fulvestrant, Goserelin, Lanreotide, Lenalidomide, Letrozole, Leuprorelin, Medroxyprogesterone, Megestrol, Mesna, Octreotide, Stilboestrol, Tamoxifen and Thalidomide. For the avoidance of doubt, the encapsulated drug may also be fumarate or a fumarate ester, to supplement the effect of the fumarate produced by in vivo degradation of the polymersome.

Pharmaceutical Composition

The polymersome of the present invention can be formulated as a pharmaceutical composition using routine techniques known in the art. For example, pharmaceutical compositions already utilised for the formulation of polymersomes or drug-containing liposomes.

The pharmaceutical composition comprises a plurality of the polymersomes of the present invention. It also comprises one or more pharmaceutically acceptable excipients or diluents. The one or more pharmaceutically acceptable excipients or diluents may be any suitable excipients or diluents. The pharmaceutical composition is typically aqueous, i.e. it contains water (in particular sterile water).

A typical pH of the aqueous pharmaceutical composition is 7.0 to 7.6, preferably 7.2 to 7.4. Pharmaceutically acceptable buffers may be used to achieve the required pH. The pharmaceutical composition may be in the form of a sterile, aqueous, isotonic saline solutions.

Typically the pharmaceutical composition is an injectable composition, e.g. it is suitable for intravenous delivery, for example it is suitable for infusion.

Medical Use of the Polymersomes

The polymersomes of the present invention are able to target immune cells and to release fumarate in vivo.

As such, the polymersomes can be used in the treatment or prevention of disorders that are susceptible to treatment or prevention with fumarate. For example, the disease may be an inflammatory disorder. The disorder may be an immune disorder (e.g. an immune disorder associated with abnormal inflammation) or a non-immune disorder (e.g. a non-immune disorder associated with abnormal inflammation). An immune disorder may be an auto-immune disorder.

Specific examples of disorders that may be susceptible to treatment or prevention with the polymersome of the present invention include multiple sclerosis, psoriatic arthritis, rheumatoid arthritis, lupus erythematosus, psoriasis, cancer (e.g. glioblastoma multiforme, cutaneous T cell lymphoma) and obstructive sleep apnoea. Further disorders that may be susceptible to treatment or prevention with the polymersome of the present invention include HIV, atherosclerosis, stroke and ischemic heart disease.

In one aspect of the invention, the disorder is cancer. The cancer may be prostate cancer, brain cancer, breast cancer, colorectal cancer, pancreatic cancer, ovarian cancer, lung cancer, cervical cancer, liver cancer, head/neck/throat cancer, skin cancer, bladder cancer or a hematologic cancer. The cancer may take the form of a tumour or a blood born cancer. The tumour may be solid. The tumour is typically malignant and may be metastatic. The tumour may be an adenoma, an adenocarcinoma, a blastoma, a carcinoma, a desmoid tumour, a desmopolastic small round cell tumour, an endocrine tumour, a germ cell tumour, a lymphoma, a leukaemia, a sarcoma, a Wilms tumour, a lung tumour, a colon tumour, a lymph tumour, a breast tumour or a melanoma. Types of blastoma include hepatblastoma, glioblastoma (e.g. glioblastoma multiforme), neuroblastoma or retinoblastoma. Types of carcinoma include colorectal carcinoma or heptacellular carcinoma, pancreatic, prostate, gastric, esophegal, cervical, and head and neck carcinomas, and adenocarcinoma. Types of sarcoma include Ewing sarcoma, osteosarcoma, rhabdomyosarcoma, or any other soft tissue sarcoma. Types of melanoma include Lentigo maligna, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Melanoma with small nevus-like cells, Melanoma with features of a Spitz nevus and Uveal melanoma. Types of lung tumour include tumours of non-small-cell lung cancer (adenocarcinoma, squamous-cell carcinoma and large-cell carcinoma) and small-cell lung carcinoma.

Examples of cancer are leukemia and lymphoma. Particular examples of leukemia include Acute lymphoblastic leukemia (ALL) (including precursor B acute lymphoblastic leukemia, precursor T acute lymphoblastic leukemia, Burkitt's leukemia and acute biphenotypic leukemia), Chronic lymphocytic leukemia (CLL), Acute myelogenous leukemia (AML) (including acute promyelocytic leukemia, acute myeloblastic leukemia, and acute megakaryoblastic leukemia), Chronic myelogenous leukemia (CIVIL) (including chronic myelomonocytic leukemia), Hairy cell leukemia (HCL), T-cell prolymphocytic leukemia (T-PLL) and Large granular lymphocytic leukemia and Adult T-cell leukemia. Lymphoma includes both Hodgkin's lymphoma (HL) and non-Hodgkin lymphoma (NHL). Examples of Hodgkin's lymphoma include Nodular sclerosing lymphoma, Mixed-cellularity subtype lymphoma, Lymphocyte-rich lymphoma and Lymphocyte depleted lymphoma. The non-Hodgkin's lymphoma includes low grade and high grade non-Hodgkin's lymphoma. Specific examples include Follicular lymphoma, Mantle cell lymphoma, Marginal zone lymphoma (including Extranodal marginal zone lymphoma/mucosa associated lymphoid tissue lymphoma/MALT lymphoma, Nodal marginal zone lymphoma and Splenic marginal zone lymphoma), Small lymphocytic lymphoma, Lymphoplasmacytic lymphoma (including Waldenstrom's macroglobulinaemia), Skin lymphomas (such as cutaneous T cell lymphoma, e.g. Mycosis fungoides), Diffuse large B cell lymphoma (DLBCL), Burkitt's lymphomas (including Burkitt like lymphomas), peripheral T cell lymphoma (including peripheral T cell lymphoma not otherwise specified (PTCL-NOS), anaplastic large cell lymphoma (ALCL), and angio immunoblastic T cell lymphoma (AITL)), Lymphoblastic lymphoma, Blastic NK cell lymphoma, Enteropathy associated T cell lymphoma (EATL), Hepatosplenic gamma delta T cell lymphoma, and Treatment related T cell lymphomas. One particular subtype of cancer is cutaneous T cell lymphoma.

Medical uses and methods of treatment, of course, involve the administration of a therapeutically effective amount of the polymersome. A therapeutically effective amount of the polymersomes is administered to a patient. A typical dose is from 0.001 to 1000 mg, measured as a weight of the polymersomes, according to the activity of the specific polymersome, the age, weight and conditions of the subject to be treated, the type and severity of the disease and the frequency and route of administration. Preferably, daily dosage levels are from 0.001 mg to 4000 mg.

EXAMPLES

Example 1

Synthetic vesicles were made using amphiphilic copolymers made by poly(propyl fumarate) (PPF) as a hydrophobic block and poly(2-(methacryloyloxy)ethyl phosphorylcholine) (PMPC) as a hydrophilic block.

A new synthetic route was developed for the production of a diblock PMPC-PPF copolymer and its assembly into vesicles was studied. It was shown that PMPC-PPF copolymer degrades very quickly into fumarate and propyl glycol (a metabolite, which is quickly (half life 2 hr) metabolized by the liver to form lactate, acetate, and pyruvate). It was thus proven that PMPC-PPF forms polymersomes that degrade over time to release large doses of fumarate.

The ability of PMPC-PPF to moderate inflammation was tested using human monocytes-derived macrophages (THP-1) stimulated with bacterial lipopolysaccharide (LPS) for 24 hours (known to induce inflammation in vitro). The media containing the LPS were removed, washed with PBS 3 times, and the macrophages incubated with PMPC-PPF for 24 hours (control cells were grown in media without any supplement of polymersomes). The decreased levels of inflammation activity were screened by Real Time quantitative PCR (qPCR, method below), with the aim to quantify the expression of a panel of genes codifying for inflammatory cytokines.

Specific cytokines tested were CCL3, CCL4, IL-1B, IL-6, IL-8, and TNF-alpha. The CCL3 and CCL4 are two of the major form of the Macrophage Inflammatory Proteins (MIP). These are chemotactic cytokines responsible for the activation and recruitment granulocytes, and they also promote the production/release of other pro-inflammatory cytokines (e.g., IL-1 and TNF-alpha). IL-1B is involved cell proliferation, differentiation, and apoptosis, while IL-6 and TNF-alpha regulate body temperature and are important mediators of the acute phase response.

The data demonstrated that the formulations are able significantly to decrease the expression level of all the inflammatory cytokines, demonstrating that they are strong candidates for treatment of inflammatory disorders.

Production of Polymersomes
Synthesis of PMPC-PPF
Example of Copolymerization Procedure: In a glovebox, 0.020 mmol SalenCrCl and 4.0 mmol maleic anhydride were placed in a vial equipped with a stir bar. The appropriate solvent (toluene, 0.50 mL) was added, followed by 4.0 mmol propylene oxide (epoxide). The vial was sealed with a Teflon lined cap, removed from the glovebox, and placed in an aluminum heat block preheated to the desired temperature (45° C.). 1H NMR spectrum analysis was used to determine the monomer conversion after the reaction became viscous. The viscous reaction mixture was then dissolved in a minimum amount of dichloromethane and precipitated into an excess of hexanes. This process was repeated (diethyl ether was used as the non-solvent in the case of PPM) until all residual monomer was removed. After polymer washes, the material was collected and vacuum dried.

Example Isomerization Procedure: For a one-pot procedure, 0.1 equivalent of diethyl amine was added directly to the polymer mixture at the end of the polymerization and the polymer was dissolved in CDCl$_3$. For a two-step procedure, an isolated polymer sample was dissolved in CDCl$_3$ and 0.1 equivalent of diethyl amine was added. For both procedures, the solution was allowed to stir and isomerization progress was checked by $^1$H NMR spectroscopy. Upon completion of the reaction, all volatiles were removed under vacuum. The polymer was subsequently redissolved in CH$_2$Cl$_2$ and precipitated into hexanes. The polymers were then vacuum dried and isomerization completion was confirmed by $^1$H NMR spectroscopy.

Example of synthesis of PPF ATRP Macroinitiator: A solution of PPF (polypropylene fumarate, 1 eq.) and triethylamine (3 eq.) in anhydrous THF was slightly cooled in an ice-water bath. Then, 2-bromoisobutyryl bromide (4 eq.) in the minimum amount of anhydrous THF was added dropwise to the reaction mixture. The solution was warmed to room temperature and stirred for 48 h. The mixture was poured into water and extensively dialysed with a 1000 kDa MWCO membrane against water and then freeze-dried.

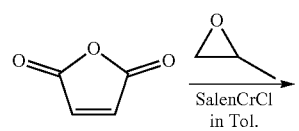

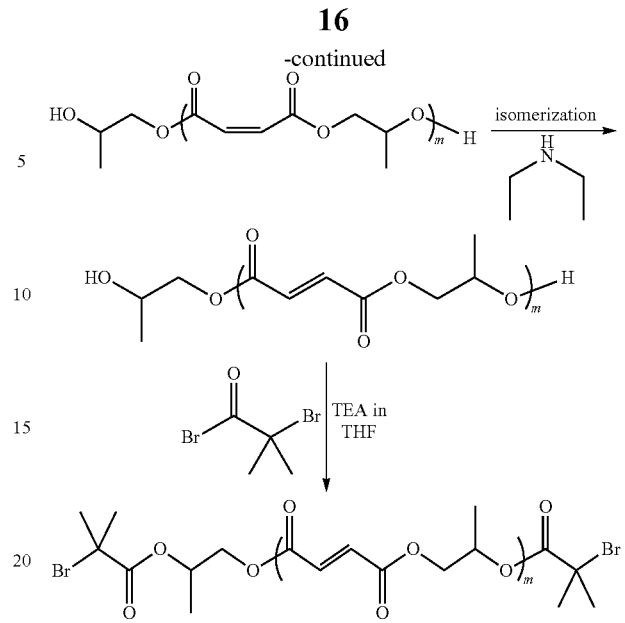

Example of synthesis of PMPC-PPF via ATRP: PPF macroinitiator (1 eq.) and MPC monomer (5 eq.) were weighed off in a round-bottom flask and dissolved in the minimum amount of EtOH, then degassed via purging for at least 30 min with N2 and placed at 30° C. After degassing, Cu(I)Br catalyst (2 eq.) and bipyridin ligand (4 eq.) are mixed as solids and added to the mixture. The progress of the reaction was monitored via $^1$H-NMR. After the polymerisation process, the mixture was opened to the air and diluted with EtOH, then passed through a silica plug to remove the copper salts. The solution obtained was concentrated via rotary evaporation and extensively dialysed with a 1000 kDa MWCO membrane against dichloromethane, then methanol and finally water. The product was then isolated via freeze-drying and characterised via 1H-NMR and GPC.

Polymersomes preparation: Thin copolymer films of PMPC-PPF dissolved in chloroform/methanol were obtained under vacuum in glass vials. Film rehydration in pH 7.4 PBS occurred over 30 days at 25° C. to form polymersomes. Polymersomes were purified from aggregates and micelles via gel permeation chromatography (GPC) using sepharose 4B as a substrate. Dynamic light scattering (DLS) was used to assess the size distribution of polymersomes, via a Malvern Zetasizer Nano ZS laser light scatterer equipped with a He—Ne 4 mW 633 nm laser. Polymersomes were diluted in filtered PBS in 1 ml disposable cuvettes, and experiments were an average of n=3 runs at a set angle of 173°. Polymersomes in filtered PBS were also assessed for morphology using transmission electron microscopy (TEM). Samples were mounted on glow-discharged carbon coated grids by submerging the grids into the polymersome solution for 60 seconds, followed by staining for 5 seconds using 0.75% (w/w) phosphotungstic acid (PTA). Grids were then washed with PBS, dried under vacuum and assessed via a JEOL microscope using 100 kV voltage tension.

Figure 2:
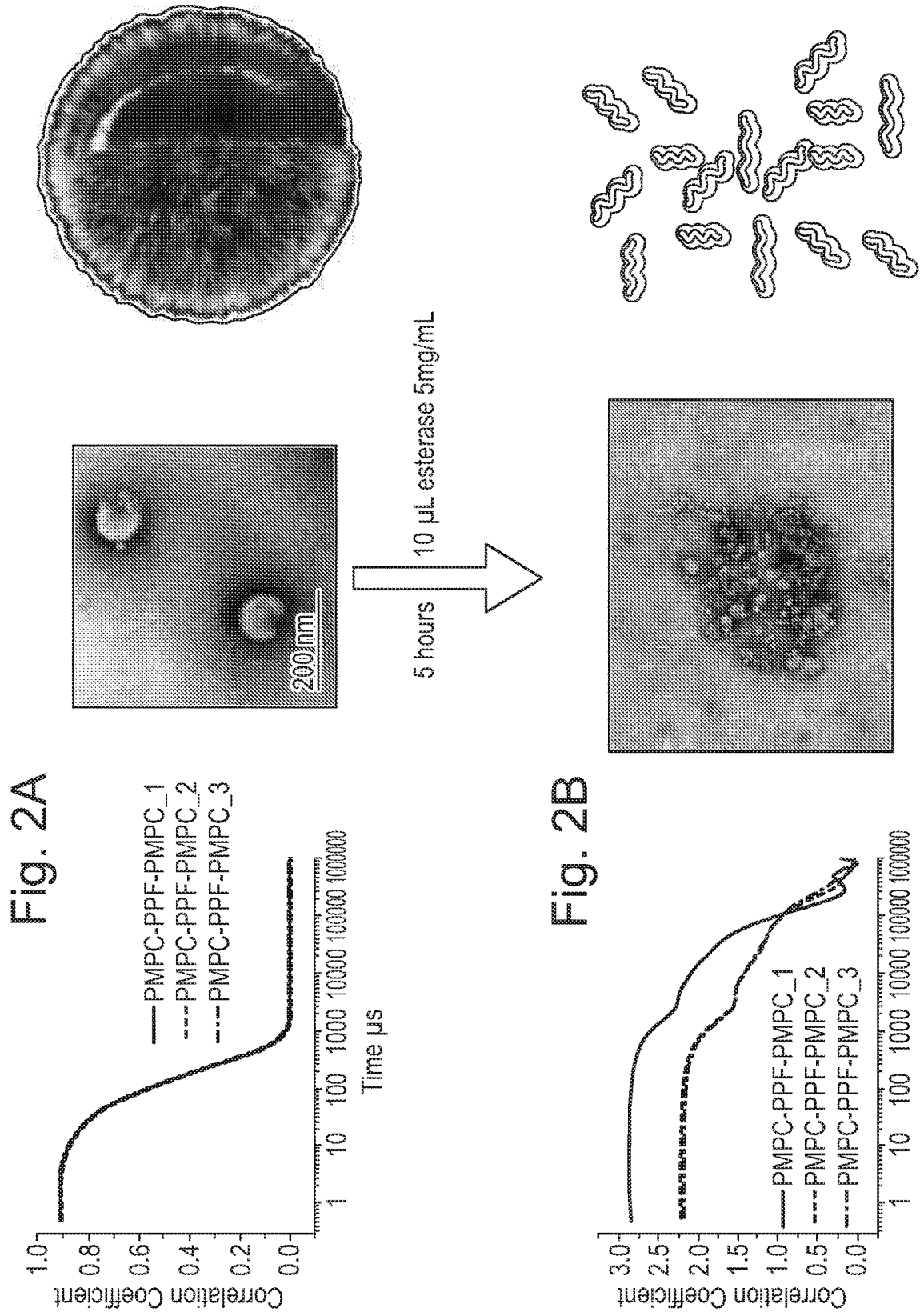
FIG. 2 shows the results of a degradation assay for the PMPC-PPF polymersome as described in Example 1.

PMPC-PPF degradation assay: PMPC-PPF polymersomes at 2 mg/ml were left stirring for 32 days with DLS checks every week to see whether something changes. After 32 days stirring of PMPC-PPF, FIG. 2, (A) DLS and TEM data, were collected and showed the presence of polymersomes with no evidence of degradation. The same sample was treated with 10 μl of esterase 5 mg/ml (B). The esterase-treated sample turned more turbid almost immediately. The first check via DLS and TEM was after 5 h and showed a clear degradation of the polymer.

qPCR

Human monocytes cells (THP-1, $1\times10^6$ cells/mL) were incubated with 5 nM of phorbol 12-myristate 13-acetate (PMA, Sigma) for 48 hours to induce differentiation to macrophages. These monocyte-derived macrophages were seeded in a 6 wells plate and then incubated with 100 ng/mL bacterial lipopolysaccharide (LPS, Sigma) to induce the over-expression of chemokines. Cells were then treated with PEG-PPF and PMPC-PPF polymersomes at a final concentration of 0.5 mg/mL for 24 hours in order to check their ability to decrease chemokines expression after LPS treatment. Untreated cells were used as control. Upon the different treatments, cells were then lysed with radio-immunoprecipitation assay (RIPA) buffer (20 mmol/L Tris, pH 7.5, 150 mmol/L NaCl, 1% Nonidet P-40, 0.5% sodium deoxycholate, 1 mmol/L EDTA, 0.1% SDS) (Sigma-Aldrich®), containing complete mini protease inhibitors (Roche®).

Total RNA was collected by using RNeasy Mini Kit (Qiagen). RNA concentration was measured with NanoDrop spectrophotometer. Complementary DNA (cDNA) was synthesised from every 1 μg of total mRNA in 20 μL volume per tube with QuantiTect Rev Transcription Kit (Qiagen). The samples were then run in a standard agarose gel (1%).

For the PCR analyses, GAPDH was used as a reference gene, and the following primers were used for analyzing the expression of specific chemokines.

Quantitative analysis was assessed with QuantiTect SYBR Green RT-qPCR Kit (Qiagen). The amplification process was done in 20 μL/tube, using the following steps: 95° C. for 5 min to make active the DNA Polymerase, followed by 40 cycles of 95° C. (10 seconds) for denaturation, and 60° C. (30 seconds) for combined annealing and extension for all primers.

These are chemotactic cytokines responsible for the activation and recruitment granulocytes, and they also promote the production/release of other pro-inflammatory cytokines (e.g., IL-1 and TNF-alpha) [Ren M, L et al. EMBO J. 29, 3952-66 (2010)]. IL-1B is involved cell proliferation, differentiation, and apoptosis, while IL-6 and TNF-alpha regulate body temperature and are important mediators of the acute phase response. FIG. 1 shows the results of this experimental setup, i.e. the real time quantitative PCR for quantifying the expression levels of cytokines. LPS=cell treated with LPS, and grown in normal media (control). PEG-DMF and MPC-DMF (i.e. PEG-PPF and PMPC-PPF) =cells treated with LPS, and then incubated with polymersomes.

The data demonstrated that the polymersome of the invention is able to significantly decrease the expression level of all the inflammatory cytokines, demonstrating that it is a strong candidate for their application in inflammatory related diseases.

Example 2

Cytotoxicity and Up-take of PMPC-PPF Loaded with Doxorubicin

Methods

PPF-polymersomes and DOXO-loaded PPF Polymersomes:

PMPC-PPF was solubilized with or without doxorubicin in organic mixture of Chloroform and methanol. The solvent was evaporated under vacuum conditions and then PBS was added to a final concentration of polymer of 5 mg/ml. The polymersomes formation was obtained by film hydration with incorporation of doxorubicin (in the samples where the drug was added). After 4 weeks the vesicles were characterised for size (dynamic light scattering), shape (transmission electron microscopy) and encapsulation efficiency.

THP-1 Cells Preparation:

Human monocytes (THP-1 cell line) were cultured at 37° C. under 5% $CO_2$ for 2-3 days in flasks with RPMI-1640 medium, supplemented with 10% foetal bovine serum and 10 mM of HEPES buffer. THP-1 (suspended) cells were then differentiated in a 96 wells plate into a macrophages phenotype (adherent cells), by incubating them with PMA for 72 hours at 37° C. The medium has than been removed and replaced with media without PMA and supplemented with PPF-polymersomes or DOXO-loaded PPF-polymersomes (or PBS for negative control) at a final concentration of 1 mg/mL.

Cytotoxicity Assay:

For the cytotoxicity assay after 24 hours incubation, Thiazolyl Blue Tetrazolium Bromide (Sigma) was added to cells at a final concentration of 0.5 mg/mL, and then the reduced formazane salt was re-suspended in acidified isopropanol. The absorbance of the solutions was measured at a UV plate reader (ELx 800 Biotek). Cell viability was then quantified by normalizing the signal to the control (untreated) cells.

Confocal Images:

For the imaging investigation, THP-1 cells were plated on a glass bottom petri dish, and then incubated with 0.1 mg/mL of DOXO-loaded PPF polymersomes for 8 hours. Images were acquired with a Leica SP8 confocal microscopy using the 570 lasers.

Results

Figure 3:
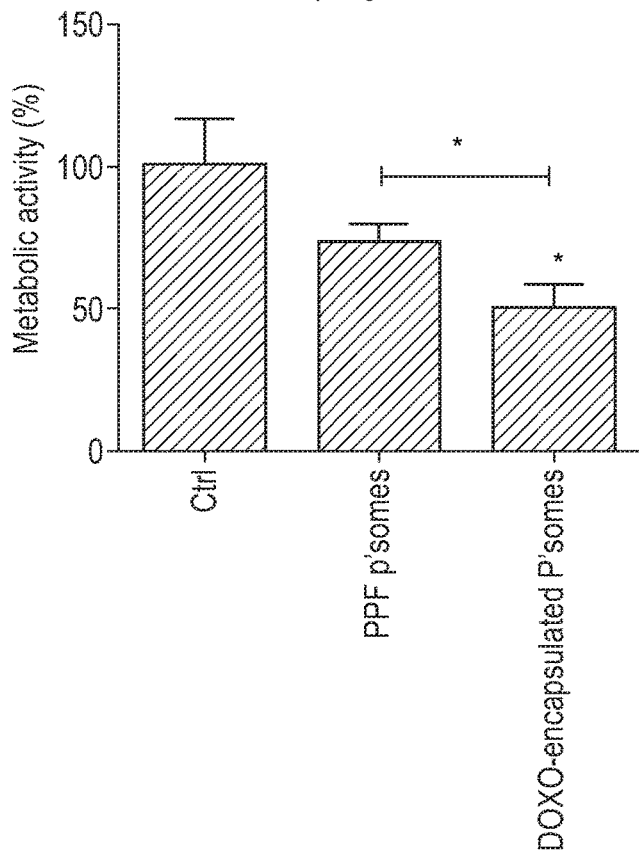
FIG. 3 shows the viability of THP-1 cells according to their metabolic activity in a control medium, in the presence of non-encapsulated polymersomes and in the presence of doxorubicin-encapsulated polymersomes, as described in Example 2.
Figure 4A:
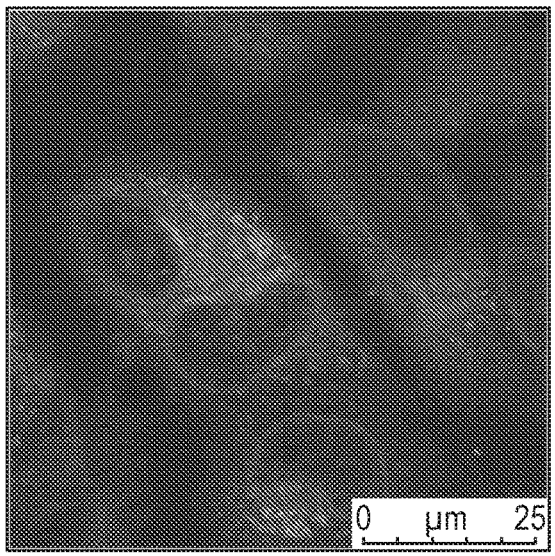
FIG. 4 shows in panels (a) and (b) (corresponding to repetitions of the same experiment) doxorubicin (grey spots) released by PMPC-PPF polymersomes into human macrophages (THP-1 cells) as described in Example 2.
Figure 4B:
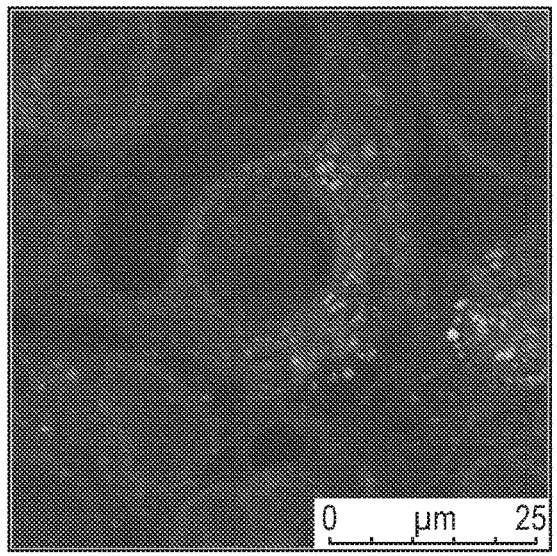

The results, shown in FIGS. 3 and 4, indicate that DOXO-PPF-polymersomes efficiently reduce the viability of cancer THP-1 cells.

The invention claimed is:

1. A polymersome that comprises an amphiphilic block copolymer comprising a hydrophilic block and a hydrophobic block, wherein:
   (a) the hydrophilic block comprises a phosphorylcholine polymer; and
   (b) the hydrophobic block comprises a fumarate polymer;

further wherein the polymersome is configured to release fumarate as an active agent at a desired site of action by in situ hydrolysis.

2. The polymersome of claim 1, wherein the phosphorylcholine polymer is an acrylate polymer.

3. The polymersome of claim 2, wherein the acrylate polymer comprises units of formula (I)

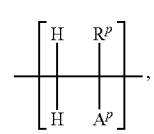

in which $R^p$ is hydrogen or methyl and $A^p$ is a group of formula (I')

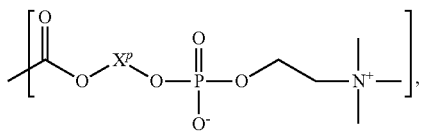

in which $X^p$ is a $C_{1-6}$ alkylene group.

4. The polymersome of claim 1, wherein the phosphorylcholine polymer is poly(2-(methacryloyloxy)ethyl phosphorylcholine).

5. The polymersome of claim 1, wherein the fumarate polymer comprises a fumarate unit of formula (II)

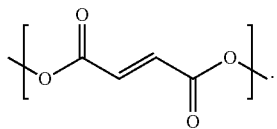

6. The polymersome of claim 1, wherein the fumarate polymer comprises repeating units of formula (III)

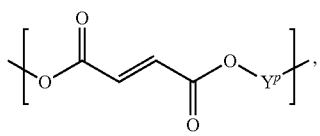

wherein $Y^p$ is a straight chain or branched $C_{1-6}$ alkylene group.

7. The polymersome of claim 1, wherein the fumarate polymer is poly(propylene fumarate).

8. The polymersome of claim 1, which further comprises a drug encapsulated within the polymersome.

9. The polymersome of claim 8, wherein the drug is an immunomodulator.

10. The polymersome of claim 8, wherein the drug is an anti-cancer compound.

11. A pharmaceutical composition comprising: a plurality of polymersomes; and one or more pharmaceutically acceptable excipients or diluents; wherein each polymersome of the plurality of polymersomes comprises an amphiphilic block copolymer comprising a hydrophilic block and a hydrophobic block, wherein:
(a) the hydrophilic block comprises a phosphorylcholine polymer; and
(b) the hydrophobic block comprises a fumarate polymer;
further wherein each polymersome of the plurality of polymersomes is configured to release fumarate as an active agent at a desired site of action by in situ hydrolysis.

12. A method comprising administering a therapeutically effective amount of a polymersome to a subject, wherein the polymersome comprises an amphiphilic block copolymer comprising a hydrophilic block and a hydrophobic block, wherein:
(a) the hydrophilic block comprises a phosphorylcholine polymer; and
(b) the hydrophobic block comprises a fumarate polymer;
further wherein the method comprises the release of fumarate as an active agent from the polymersome at a desired site of action by in situ hydrolysis.

* * * * *